(12) United States Patent  (10) Patent No.: US 8,208,141 B2
Schmidt et al.  (45) Date of Patent: Jun. 26, 2012

(54) INSPECTION SYSTEMS AND METHODS FOR BLOW-MOLDED CONTAINERS

(75) Inventors: William E. Schmidt, Gibsonia, PA (US); Georg V. Wolfe, Butler, PA (US)

(73) Assignee: AGR International, Inc., Butler, PA (US)

( * ) Notice: Subject to any disclaimer, the term of this patent is extended or adjusted under 35 U.S.C. 154(b) by 0 days.

(21) Appl. No.: 13/044,390

(22) Filed: Mar. 9, 2011

(65) Prior Publication Data

US 2012/0018925 A1  Jan. 26, 2012

Related U.S. Application Data

(63) Continuation of application No. 12/310,263, filed as application No. PCT/US2007/019230 on Aug. 31, 2007, now Pat. No. 7,924,421.

(60) Provisional application No. 60/841,954, filed on Sep. 1, 2006.

(51) Int. Cl.
*G01J 3/46* (2006.01)

(52) U.S. Cl. .............. 356/402; 250/223 B; 264/408

(58) Field of Classification Search ........... 356/239.4, 356/402; 250/223 B; 264/408
See application file for complete search history.

(56) References Cited

U.S. PATENT DOCUMENTS

| | | | |
|---|---|---|---|
| 3,439,178 A | 4/1969 | Rottmann | |
| 3,456,788 A | 7/1969 | Stapf et al. | |
| 3,729,632 A | 4/1973 | Cho et al. | |
| 3,827,812 A | 8/1974 | Heimann | |
| 3,923,158 A | 12/1975 | Fornåå | |
| 3,980,890 A | 9/1976 | Heckrodt et al. | |
| 4,304,995 A | 12/1981 | Huttunen et al. | |
| 4,332,606 A | 6/1982 | Gardner | |
| 4,393,305 A | 7/1983 | Shimizu et al. | |
| 4,476,533 A | 10/1984 | Daudt et al. | |
| 4,490,612 A | 12/1984 | Törmälä | |
| 4,639,263 A | 1/1987 | Kulikauskas | |
| 4,691,830 A | 9/1987 | Ahl et al. | |
| 4,762,544 A | 8/1988 | Davey | |

(Continued)

FOREIGN PATENT DOCUMENTS

DE  3611536 A1  10/1987

(Continued)

OTHER PUBLICATIONS

International Search Report, PCT Application No. PCT/US2007/019230 dated Mar. 19, 2008 (3 pages).

(Continued)

*Primary Examiner* — Kara E Geisel
(74) *Attorney, Agent, or Firm* — K&L Gates LLP

(57) ABSTRACT

Systems and methods for in-line inspection of plastic blow molded containers. The inspection system may comprise a plurality of emitter assemblies arranged in a vertical array. Each emitter assembly may cyclically emit light energy in at least two different narrow wavelength bands at a container as the container passes through an inspection area. The system may also comprise a plurality of broadband photodetectors arranged in a vertical array, each photodetector facing at least one of the emitter assemblies with the inspection area therebetween such that the photodetectors are capable of sensing light energy that passes through the container when it is in the inspection area. The system may also comprise a processor in communication with the photodetectors for determining a characteristic of the container based on signals from the photodetectors.

25 Claims, 15 Drawing Sheets

U.S. PATENT DOCUMENTS

| | | | |
|---|---|---|---|
| 4,919,534 A * | 4/1990 | Reed | 356/73 |
| 5,139,406 A | 8/1992 | Hoshino et al. | |
| 5,323,229 A | 6/1994 | May et al. | |
| 5,437,702 A | 8/1995 | Burns et al. | |
| 5,591,462 A | 1/1997 | Darling et al. | |
| 5,784,157 A | 7/1998 | Gorfinkel et al. | |
| 6,705,528 B2 | 3/2004 | Good et al. | |
| 6,753,527 B1 | 6/2004 | Yamagishi et al. | |
| 6,863,860 B1 | 3/2005 | Birckbichler et al. | |
| 6,872,895 B2 | 3/2005 | Cochran et al. | |
| 6,962,670 B1 | 11/2005 | Hanson et al. | |
| 6,967,716 B1 | 11/2005 | Cochran et al. | |
| 6,985,221 B2 | 1/2006 | Semersky et al. | |
| 7,374,713 B2 | 5/2008 | Birckbichler et al. | |
| 7,378,047 B2 | 5/2008 | Birckbichler et al. | |
| 2001/0054680 A1 | 12/2001 | Lindner | |
| 2003/0223086 A1 | 12/2003 | Semersky et al. | |
| 2004/0091011 A1 | 5/2004 | Liu | |
| 2004/0107065 A1 | 6/2004 | Al-Ali | |
| 2005/0127572 A1 | 6/2005 | Birckbichler et al. | |
| 2006/0126060 A1 | 6/2006 | Colle et al. | |
| 2008/0197542 A1 | 8/2008 | Birckbichler et al. | |

FOREIGN PATENT DOCUMENTS

| | | |
|---|---|---|
| EP | 0348524 A1 | 1/1990 |
| WO | WO 01/65204 A1 | 9/2001 |

OTHER PUBLICATIONS

International Preliminary Examination Report mailed Feb. 1, 2010 in corresponding International Application No. PCT/US2007/019230.

AGR-TOPWAVE, LLC, Pet Wall, pp. 1-2, Butler, PA, USA.

AGR-TOPWAVE, LLC, Profiler Guage PG 9800, pp. 1-4, Butler, PA USA.

Zarnick, K., "100% On-Line Inspectino for the Pet Container-Industry", SPE Conference/Plastics West, Las Vegas, NV, Oct. 4, 1990 and SPE Conference, Berlin, Germany, Oct. 22-25, 1990, pp. 1-7, Figs. 1-7 (18 pages total).

Puvak, R., "Improving Production Performance of PET Containers through the use of On-Line Inspection Systems", pp. 1-8, Figures 1-8 (19 pages total).

Tormala, S., "High Performance Plastic Packaging", Society fo Plastics Engineers International, Oct. 31-Nov. 1, 1989, pp. 1-8, 8 tests.

Adolfs, F., Esprit, KB-Musica (2671), plas. 140.KRP.1, Sep. 19, 1989, pp. 1-10, Figs, 1-5.

Puvak, R., Improving PET Production Efficiencies via on-Line Inspection and Rejection fo Defective Preforms and Finished Containers, pp. 1-10, Figs. 1-8, Sep. 24, 2002.

* cited by examiner

INSPECTION SYSTEMS AND METHODS FOR BLOW-MOLDED CONTAINERS

PRIORITY CLAIM

The present application is a continuation of U.S. patent application Ser. No. 12/310,263, file Feb. 18, 2009 now U.S. Pat. No. 7,924,421 entitled, "In-Line Inspection System for Vertically Profiling Plastic Containers Using Multiple Wavelength Discrete Spectral Light Sources," by William E. Schmidt, et al., which is incorporated by reference herein in its entirety, which is the national stage of PCT application Serial No. PCT/US07/19230, file Aug. 31, 2007 and which claims priority to U.S. provisional application Ser. No. 60/841,954, filed Sep. 1, 2006, entitled, "Measuring container characteristics using multiple wavelength discrete spectral light sources and broadband detectors," by William E. Schmidt, et al., also incorporated herein by reference in its entirety.

BACKGROUND

Measuring characteristics of plastic bottles is well known and standardized test methods for such exist within industry. For example, it is known to measure the wall thickness of a plastic bottle using a system that employs a broadband light source, a chopper wheel, and a spectrometer to measure the wall thickness of the plastic bottle as it passes between the light source and the spectrometer after being formed by a blow molder. The broadband light source in such a system provides chopped IR light energy that impinges the surface of the plastic container, travels through both walls of the container, and is sensed by the spectrometer to determine absorption levels in the plastic at discrete wavelengths. This information is used to determine characteristics of the plastic bottle, such as wall thickness. Other machines are available from several manufacturers throughout the world. Exemplary of such machines is the AGR TopWave Petwall Plus Vision system. This machine performs a thickness measurement of plastic containers by measuring the difference between a PET absorption wavelength and a non-absorption reference wavelength.

In practice, such systems use an incandescent bulb to generate broadband light within the visible and infrared spectrums of interest. The broadband light is chopped, collimated, transmitted through two walls of the plastic container, and finally divided into wavelengths of interest by the spectroscope. This sampling process is limited in both speed and response time.

The state of the art in blow molding technology continues to increase the sampling speed required. This will, in time, render the current technologies used to measure container characteristics unusable.

SUMMARY OF THE INVENTION

In one general aspect, the present invention is directed to an inspection system for inspecting blow molded plastic or PET (polyethylene terephthalate) containers. According to various embodiments, the inspection system is an in-line system that comprises a vertical array of emitter assemblies that cyclically emit light energy in at least two different narrow wavelength bands at a blow molded container as the container passes through an inspection area. For example, each emitter assembly may comprise two narrow band light sources: one that emits light energy in a narrow wavelength band that is absorbed by the material of the container in a manner highly dependent on the thickness of the material; and one that emits light energy in another, discrete narrow wavelength band that is substantially transmissive by the material of the container. The light sources may be LEDs or laser diodes, for example.

The inspection system may also comprise a vertical array of broadband photodetectors facing the emitter assemblies, such as in a 1-to-1 relationship. The light energy that is not absorbed by the container may pass through two sidewalls of the container, where the light energy is sensed by the photodetectors. Each broadband photodetector preferably has a broad enough response range to detect light energy from the different light sources of the emitter assemblies. The inspection system may also comprise a processor in communication with the photodetectors, where the processor is programmed to determine a characteristic of the inspected container, such as the average 2-wall thickness of the container or some other characteristic, based on output signals from the photodetectors. This information may be used in determining whether the container should be rejected. The processor may also be programmed to calculate real, time calibration adjustments for the emitters and sensors to maintain calibration. Further, the processor may also be programmed to send control signals to the blow molder system to adjust parameters of the blow molder, such as heating temperature or other parameters, to close a feedback control loop for the blow molder system.

According to various embodiments, the light sources in the emitter assemblies may be cyclically controlled such that during each cycle there is a time period when: only one of the light sources is on; only the other light source is on; and both light sources are off. Such a timing architecture may aid the processor in determining the characteristics of the container and for calculating the calibration adjustments.

According to various embodiments, pairs of emitters and sensors may be relatively densely spaced along the vertical span of the containers in the inspection area. Thus, a relatively complete thickness profile of the inspected container may be obtained.

These and other benefits of the invention will be apparent from the description to follow.

FIGURES

Various embodiments of the present invention are described herein by way of example in conjunction with the following figures, wherein:

FIG. 1 is simplified block diagram of a blow molder system according to various embodiments of the present invention;

FIGS. 2, 3 and 11 provide views of a portion of an inspection system according to various embodiments of the present invention;

DESCRIPTION OF INVENTION

In one general aspect, the present invention is directed to an inspection system for measuring a characteristic of a container, such as a plastic, PET, or other type of polyolefin container. As described below, the inspection system may comprise (1) multiple wavelength discrete spectral light sources with high energy output, and (2) highly sensitive broadband detectors (or sensors). The inspection system may also comprise a processor to determine the characteristic (or characteristics) of the containers based on the light energy from the light sources detected by the sensors. Such an inspection system may be used in plastic or PET container manufacturing operations operating at higher blow molder speeds. The wavelength discrete spectral light sources may comprise, for example, a number of light emitting diodes (LEDs) or laser diodes, having different, narrow band emission spectra. The characteristics measured by the system based on the ratio of the light energy absorbed by the containers at the selected wavelength ranges may include, for example, wall thickness (e.g., average 2-wall thickness) or characteristics related to wall thickness, such as mass, volume, and/or material distribution of the walls of the container. As described further below, the measured characteristics may be used to reject manufactured containers that do not meet specifications and/or for modifying parameters of the blow molder system (e.g., temperature, pressure and/or blow timing).

Figure 1:
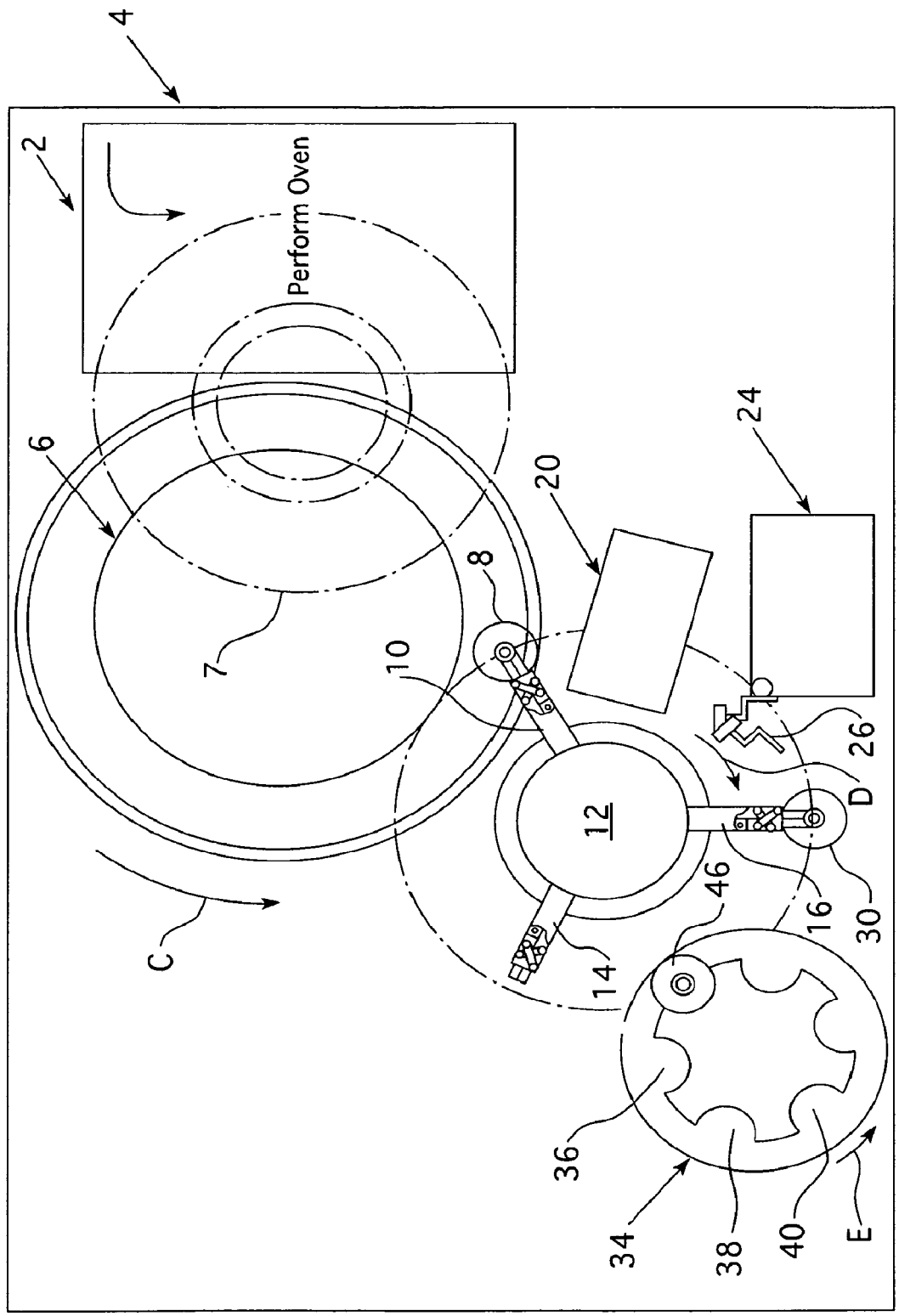

Before describing the inspection system in more detail, an overview of a blow molder system in which the inspection system may be employed is provided. FIG. 1 is a block diagram of a blow molder system 4 according to various embodiments of the present invention. The blow molder system 4 includes a preform oven 2 that typically carries the plastic preforms, from which the containers are manufactured, on spindles through the oven section so as to preheat the preforms prior to blow-molding of the containers. The preform oven 2 may comprise, for example, infrared heating lamps or other heating devices to heat the preforms above their glass transition temperature. The preforms leaving the preform oven 2 enter the blow molder 6 by means, for example, of a conventional transfer system 7 (shown in phantom).

The blow molder 6 may comprise a number of molds, such as on the order of ten to twenty-four, for example, arranged in a circle and rotating in a direction indicated by the arrow C. The preforms may be stretched in the blow molder, using air and/or a core rod, to conform the preform to the shape defined by the mold. Containers emerging from the blow molder 6, such as container 8, may be suspended from a transfer arm 10 on a transfer assembly 12, which is rotating in the direction indicated by arrow D. Similarly, transfer arms 14 and 16 may, as the transfer assembly 12 rotates, pick up the container 8 and transport the container through the inspection area 20, where it may be inspected by the inspection system described below. A reject area 24 has a reject mechanism 26 that may physically remove from the transfer assembly 12 any containers deemed to be rejected.

In the example of FIG. 1, container 30 has passed beyond the reject area 24 and may be picked up in a star wheel mechanism 34, which is rotating in direction E and has a plurality of pockets, such as pockets 36, 38, 40, for example. A container 46 is shown in FIG. 1 as being present in such a star wheel pocket. The containers may then be transferred in a manner known to those skilled in the art to conveyer means according to the desired transport path and nature of the system. According to various embodiments, the blow molder system 4 may produce containers at a rate of 20,000 to 100,000 per hour.

Figure 2:
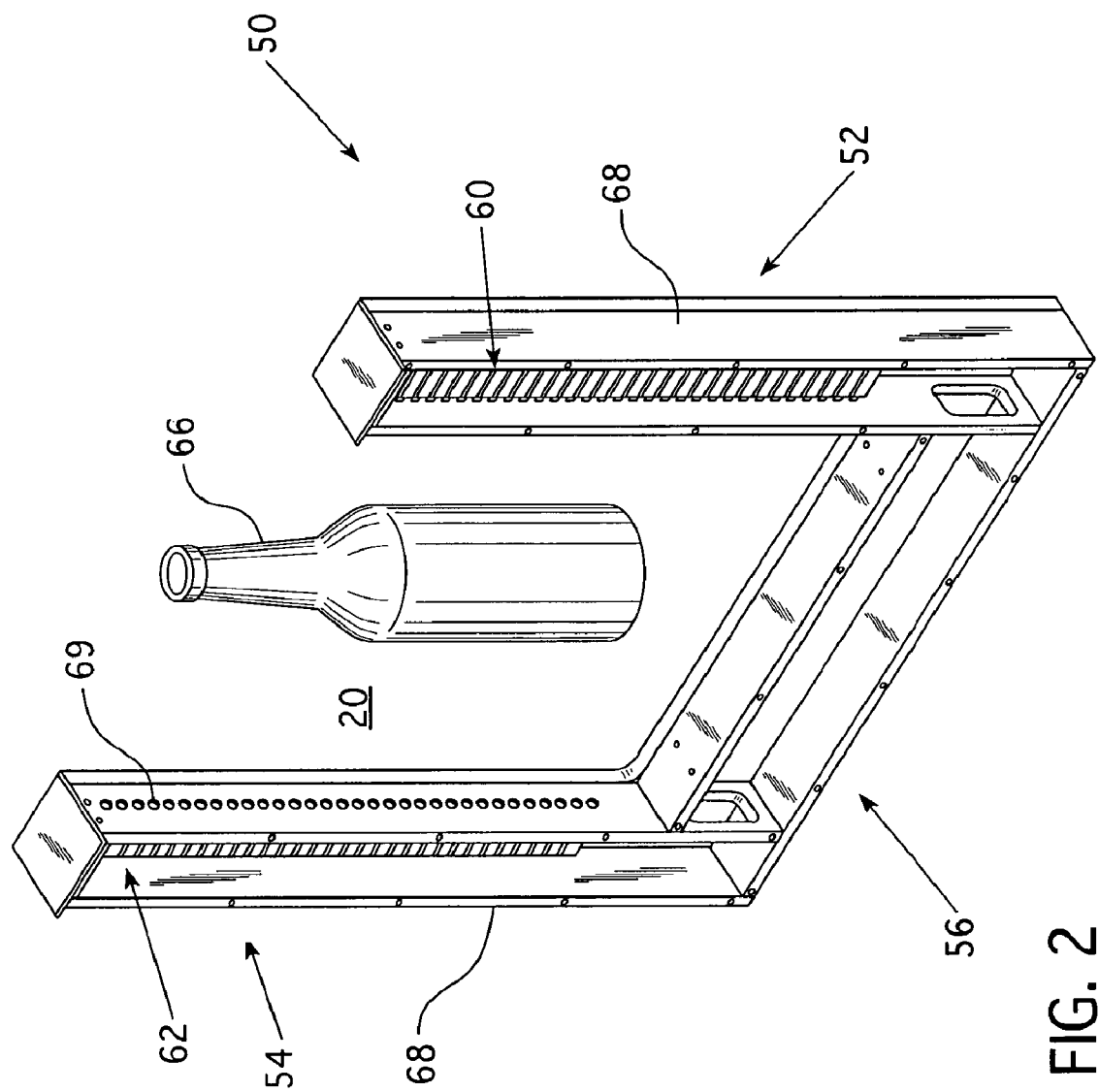
Figure 3:
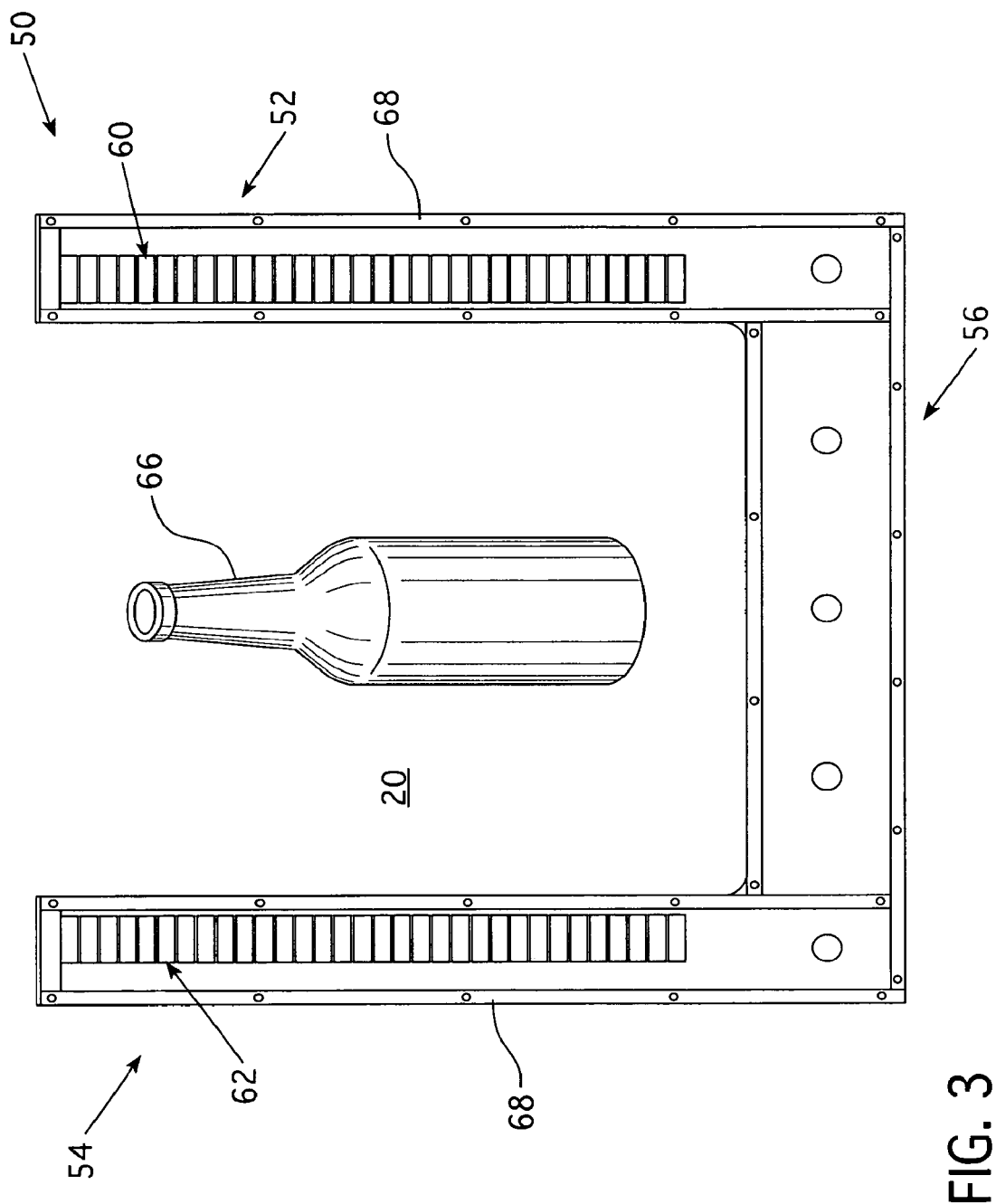

FIGS. 2 and 3 illustrate an inspection system 50 according to various embodiments of the present invention. The inspection system 50, as described further below, may be an in-line inspection system that inspects the containers as they are formed, as fast as they are formed (e.g., up to 100,00 containers per hour), without having to remove the containers from the processing line for inspection and without having to destroy the container for inspection. The inspection system 50 may determine characteristics of each container formed by the blow molder 4 (e.g., average 2-wall thickness, mass, volume, and/or material distribution) as the formed containers are rotated through the inspection area 20 by the transfer assembly 12 following blow molding. FIG. 2 is a perspective view of the inspection system 50 and FIG. 3 is a front plan view of the inspection system 50. As shown in these figures, the inspection system 50 may comprise two vertical arms 52, 54, with a cross bar section 56 therebetween at the lower portion of the arms 52, 54. One of the arms 52 may comprise a number of light energy emitter assemblies 60, and the other arm 54 may comprise a number of broadband sensors 62 for detecting light energy from the emitter assemblies 60 that passes through a plastic container 66 passing between the arms 52, 54. Thus, light energy from the emitter assembly 60 that is not absorbed by the container may pass through the two opposite sidewalls of the container 66 and be sensed by the sensors 62. The container 66 may be rotated through the inspection area 20 between the arms 52, 54 by the transfer assembly 12 (see FIG. 1). In other embodiments, a conveyor may be used to transport the containers through the inspection area 20.

According to various embodiments, the emitter assemblies 60 may comprise a pair of light emitting diodes (LEDs) that emit light energy at different, discrete narrow wavelengths bands. For example, one LED in each emitter assembly 60 may emit light energy in a narrow band wavelength range where the absorption characteristics of the material of the container are highly dependent on the thickness of the material of the plastic container 66 ("the absorption wavelength"). The other LED may emit light energy in a narrow band wavelength that is substantially transmissive ("the reference wavelength") by the material of the plastic container 66.

According to various embodiments, there may be one broadband sensor 62 in the arm 54 for each emitter 60 in the arm 52. Based on the sensed energy at both the absorption and reference wavelengths, the thickness through two walls of the container 66 can be determined at the height level of the emitter-sensor pair. This information can be used in determining whether to reject a container because its walls do not Meet specification (e.g., the walls are either too thin or too thick). This information can also be used as feedback for adjusting parameters of the preform oven 2 and/or the blow molder 6 (see FIG. 1) according to various embodiments, as described further below.

The more closely the emitter-sensor pairs are spaced vertically, the more detailed thickness information can be obtained regarding the container 66. According to various embodiments, there may be between three (3) and fifty (50) such emitter-sensor pairs spanning the height of the container 66 from top to bottom. Preferably, there are up to thirty two emitter-sensor pairs spaced every 0.5 inches or less. Such closely spaced emitter-sensor pairs can effectively provide a rather complete vertical wall thickness profile for the container 66.

According to various embodiments, when the inspection system 50 is used to inspect plastic or PET containers 66, the absorption wavelength narrow band may be around 2350 nm, and the reference wavelength band may be around 1835 nm. Of course, in other embodiments, different wavelength bands may be used. As used herein, the terms "narrow band" or "narrow wavelength band" means a wavelength band that is less than or equal to 200 nm full width at half maximum (FWHM). That is, the difference between the wavelengths at which the emission intensity of one of the light sources is half its maximum intensity is less than or equal to 200 nm. Preferably, the light sources have narrow bands that are 100 nm or less FWHM, and preferably are 50 nm or less FWHM.

The arms 52, 54 may comprise a frame 68 to which the emitter assemblies 60 and sensors 62 are mounted. The frame 68 may be made of any suitable material such as, for example, aluminum. Controllers on circuit boards (not shown) for controlling/powering the emitter 60 and sensors 62 may also be disposed in the open spaces defined by the frame 68. The crossbar section 56 may be made out of the same material as the frame 68 for the arms 52, 54.

The frame 68 may define a number of openings 69 aimed at the inspection area 20. As shown in FIG. 2, there may be an opening for each sensor 62. There may also be a corresponding opening for each emitter assembly 60. Light energy from the emitter assemblies may be directed through their corresponding opening into the inspection area 20 and toward the sensors 62 behind each opening 69.

Figure 4:
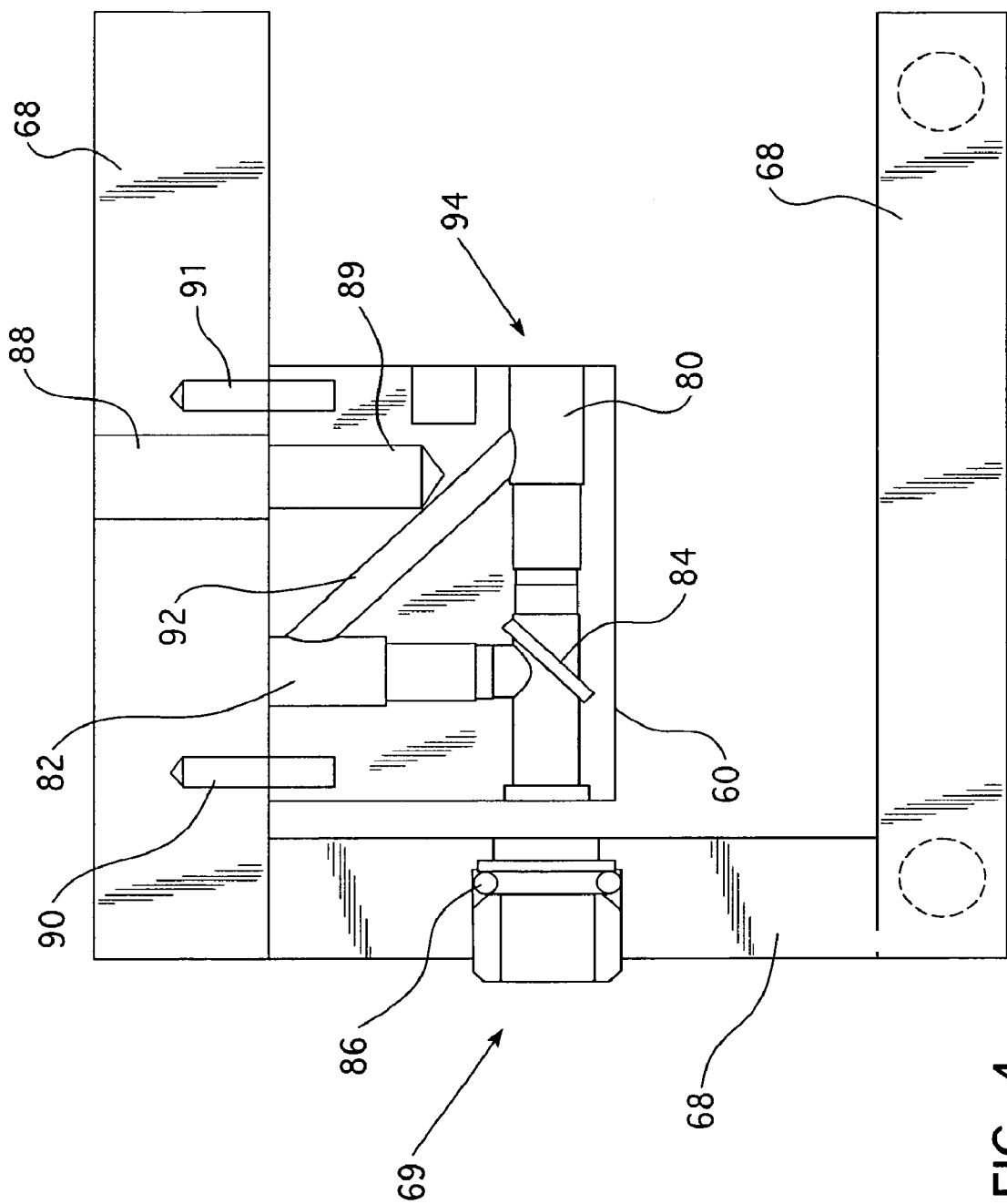
FIGS. 4 to 8 show an emitter assembly of the inspection system according to various embodiments of the present invention.

FIG. 4 is a top plan view of an emitter assembly 60 according to various embodiments of the present invention. The emitter assembly 60 may comprise a first LED contained in a first LED sleeve 80, and a second LED contained in a second LED sleeve 82 (sometimes respectively referred to as "first LED 80" and "second LED 82" for purposes of simplicity). One of the LEDs 80, 82 may emit light energy at the reference wavelength and the other may emit light energy at the absorption wavelength. According to one embodiment, the first LED sleeve 80 may contain the LED emitting at the absorption wavelength band and the second LED sleeve 82 may contain the LED emitting at the reference wavelength band.

As shown in FIG. 4, the emitter assembly 60 may comprise a beam splitter 84. The beam splitter 84 may be a dichroic beam splitter that is substantially transmissive to the light energy from the first LED 80 such that the light energy from the first LED 80 propagates toward the opening 69, and substantially reflective of the light energy from the second LED 82 such that the light energy from the second LED is also directed toward the opening 69. The assembly 60 may also comprise a covering 86 for each opening 69. The covering 86 may be substantially transmissive for the emitted wavelength bands of the first and second LEDs.

A screw (not shown) through screw openings 88, 89 may be used to secure the assembly 60 to the frame 68. Pins (not shown) in pin openings 90, 91 may be used to align the assembly 60 for improved optical performance. Conduit 92 may be used to contain electrical wires for the second LED 82, such that the wires (not shown) for both the first and second LEDs 80, 82 may attach the assembly 60 at a back portion 94 of the assembly 60.

Figure 5:
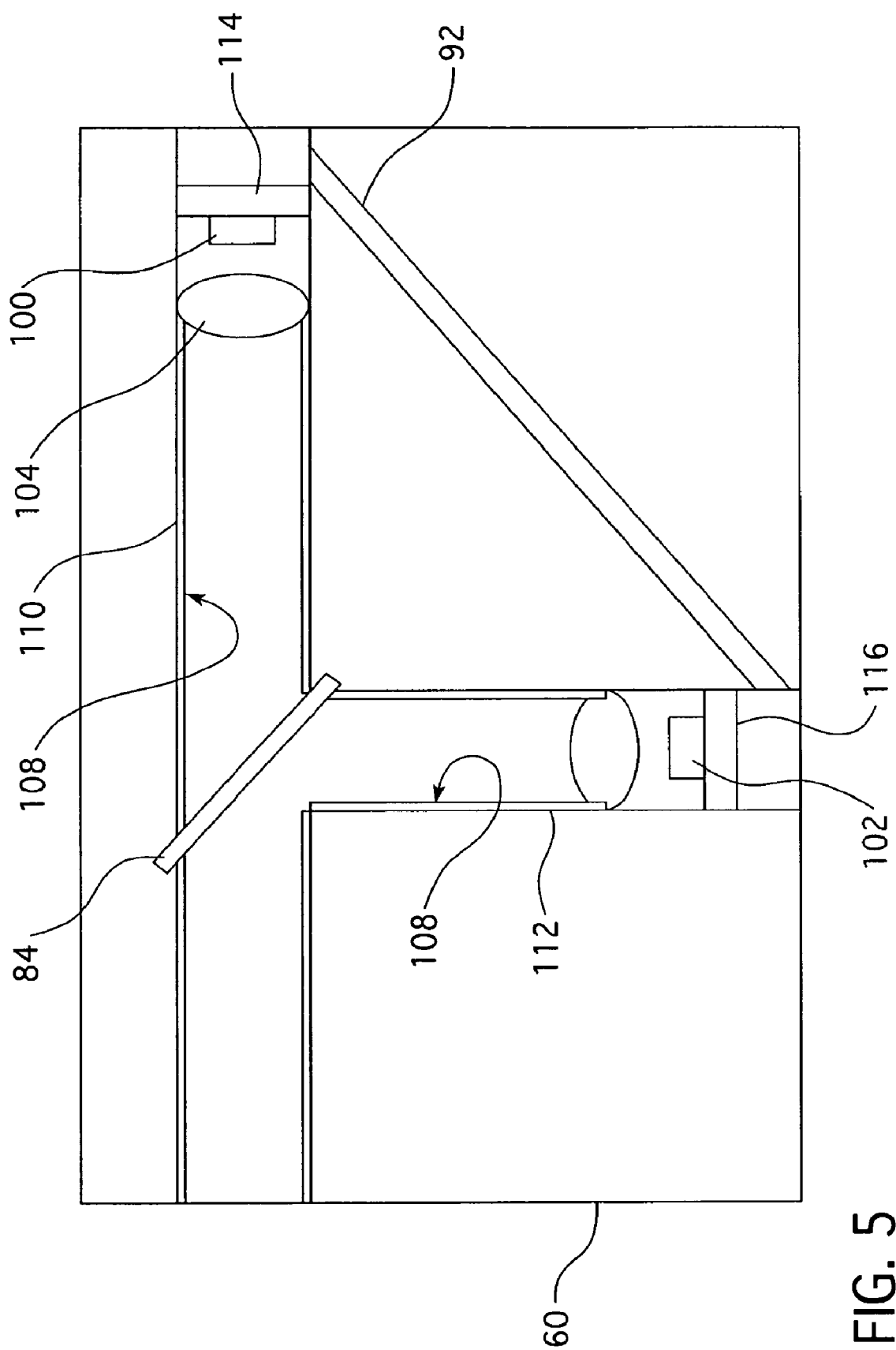

FIG. 5 provides another view of an emitter assembly 60. This figure shows the first LED 100 and the second LED 102. The light energy from each LED 100, 102 may be directed through a one or series of collection and collimating lenses 104, 106, respectively, by highly reflective interior walls 108 of a cylinder casing 110, 112 that respectively encases the LEDs and the lenses. Each LED 100, 102 may have an associated circuit board 114, 116 or other type of substrate to which the LEDs 100, 102 are mounted and which provide an interface for the electrical connections (not shown) to the LEDs 100, 102.

Figure 6:
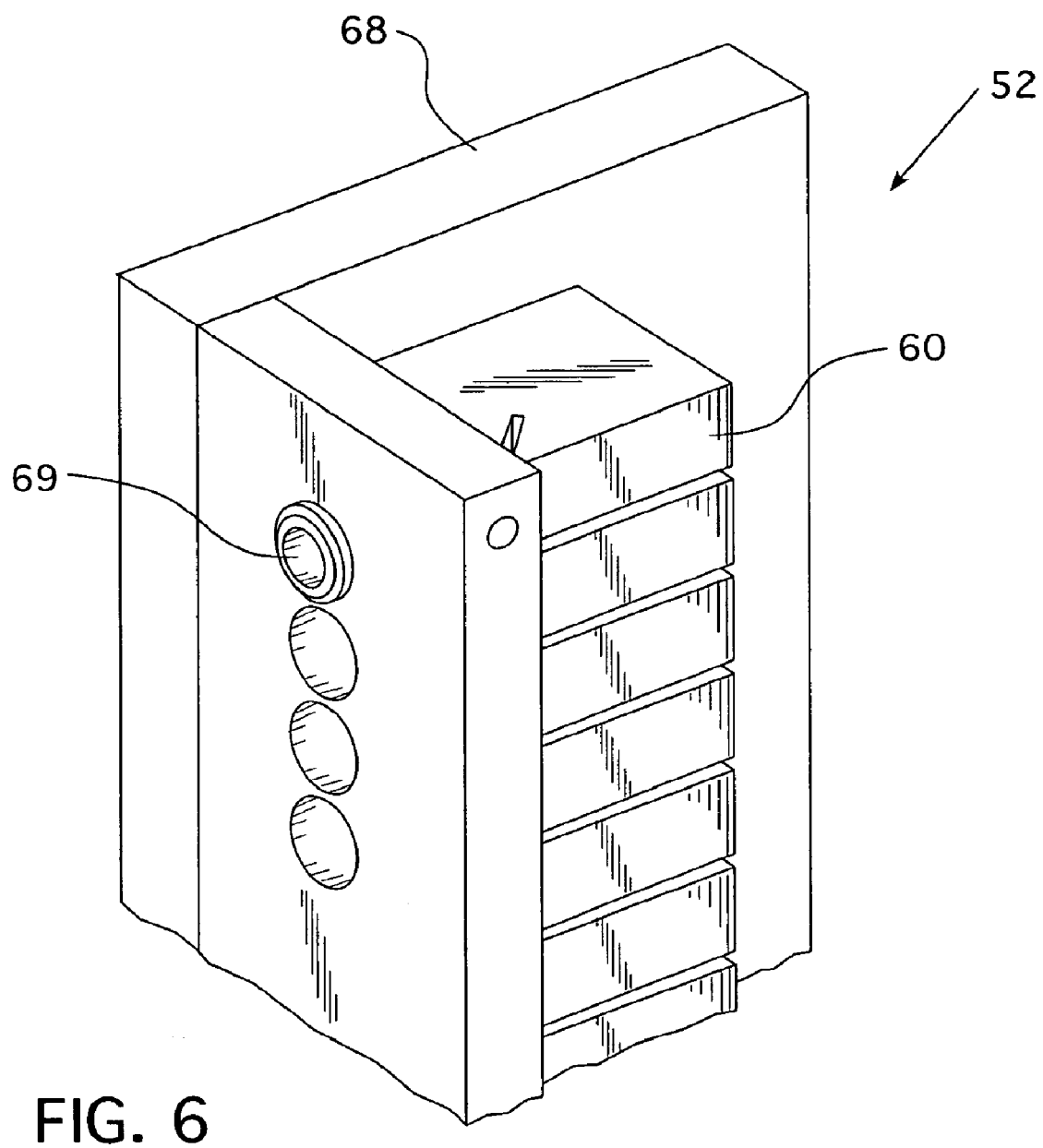
Figure 7:
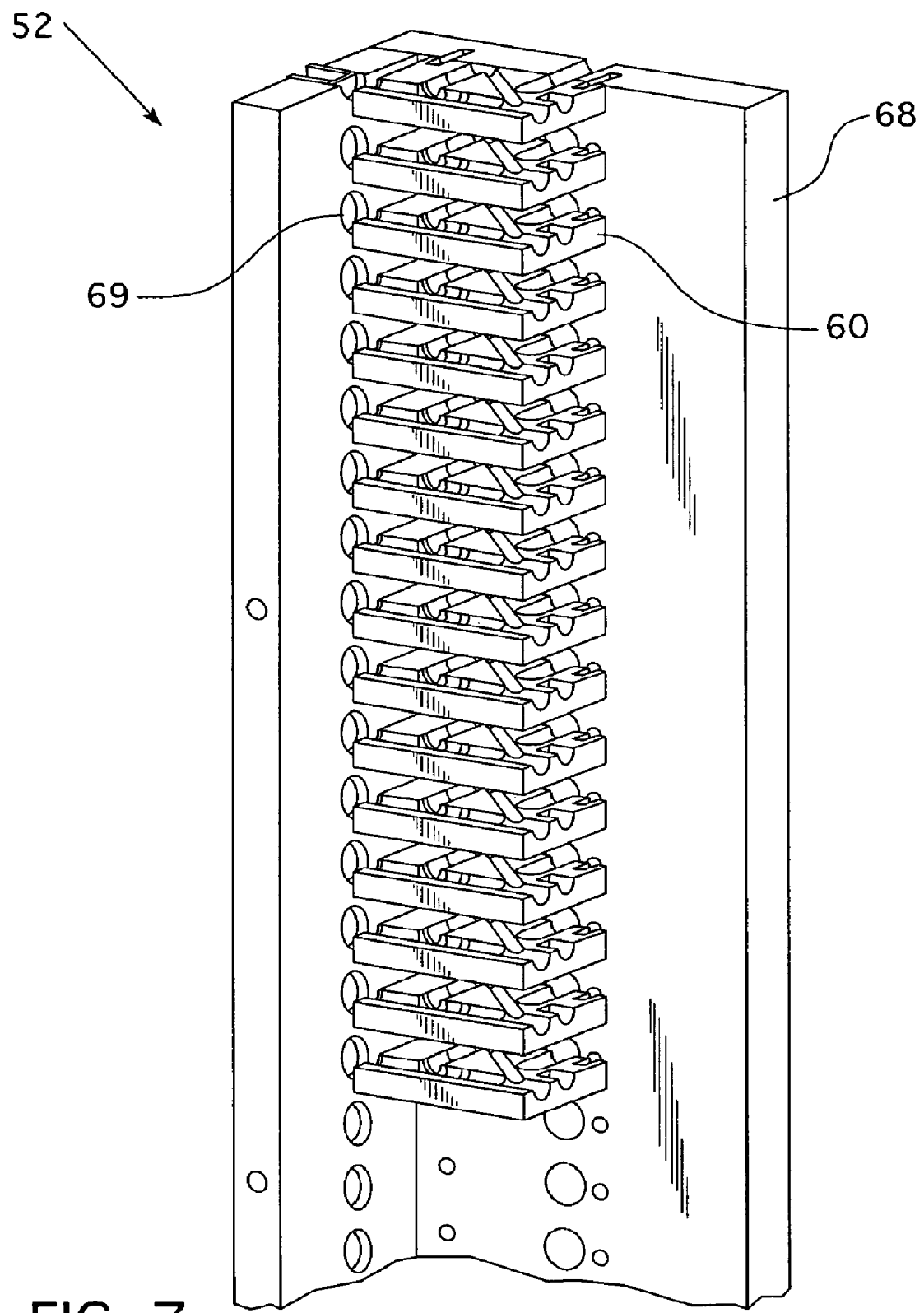
Figure 8:
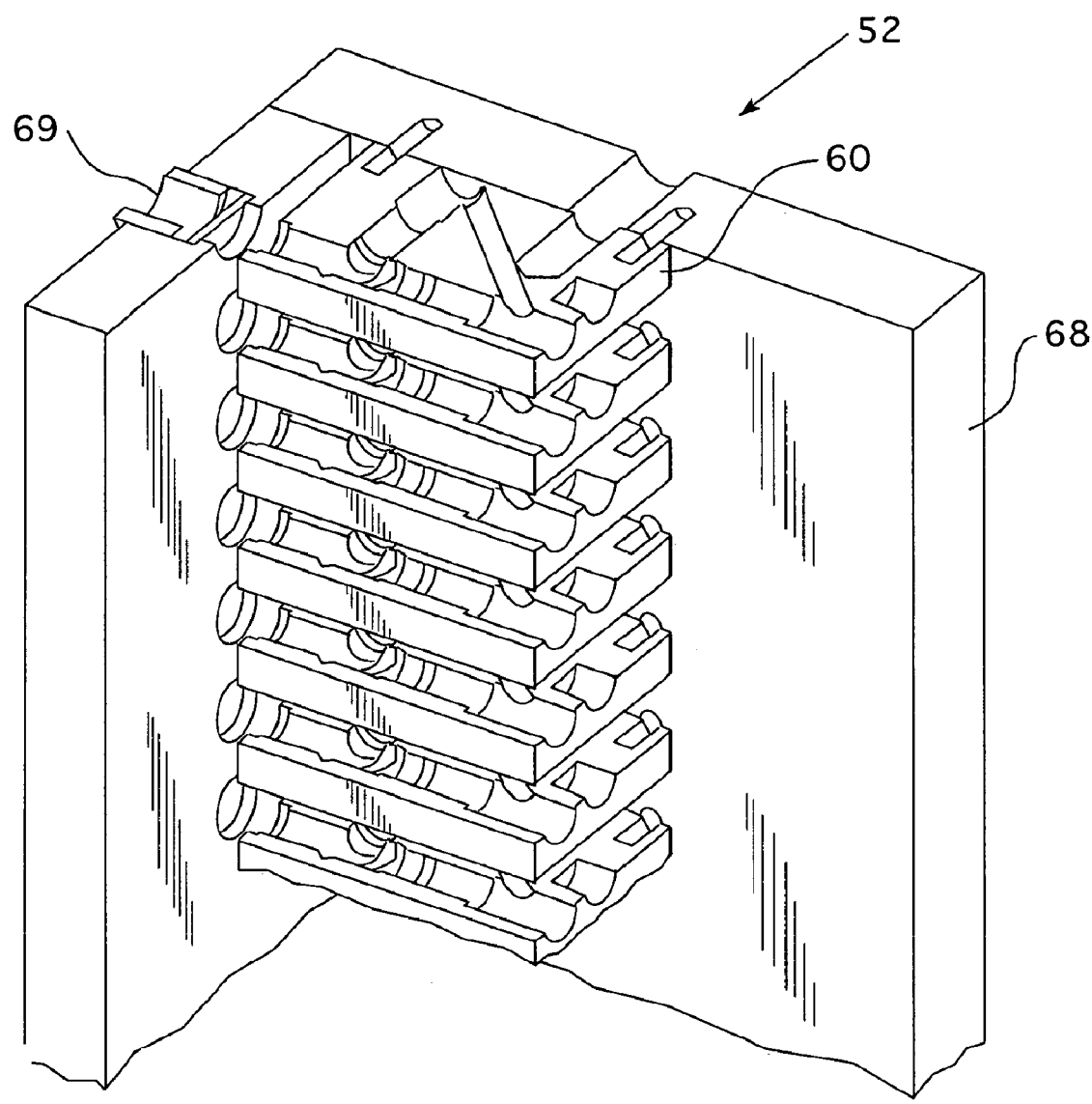

FIGS. 6-8 show different views of the emitter assemblies 60 according to various embodiments of the present invention. In FIGS. 7 and 8, only half (the lower half) of the emitter assemblies 60 are shown for illustration purposes.

Figure 9:
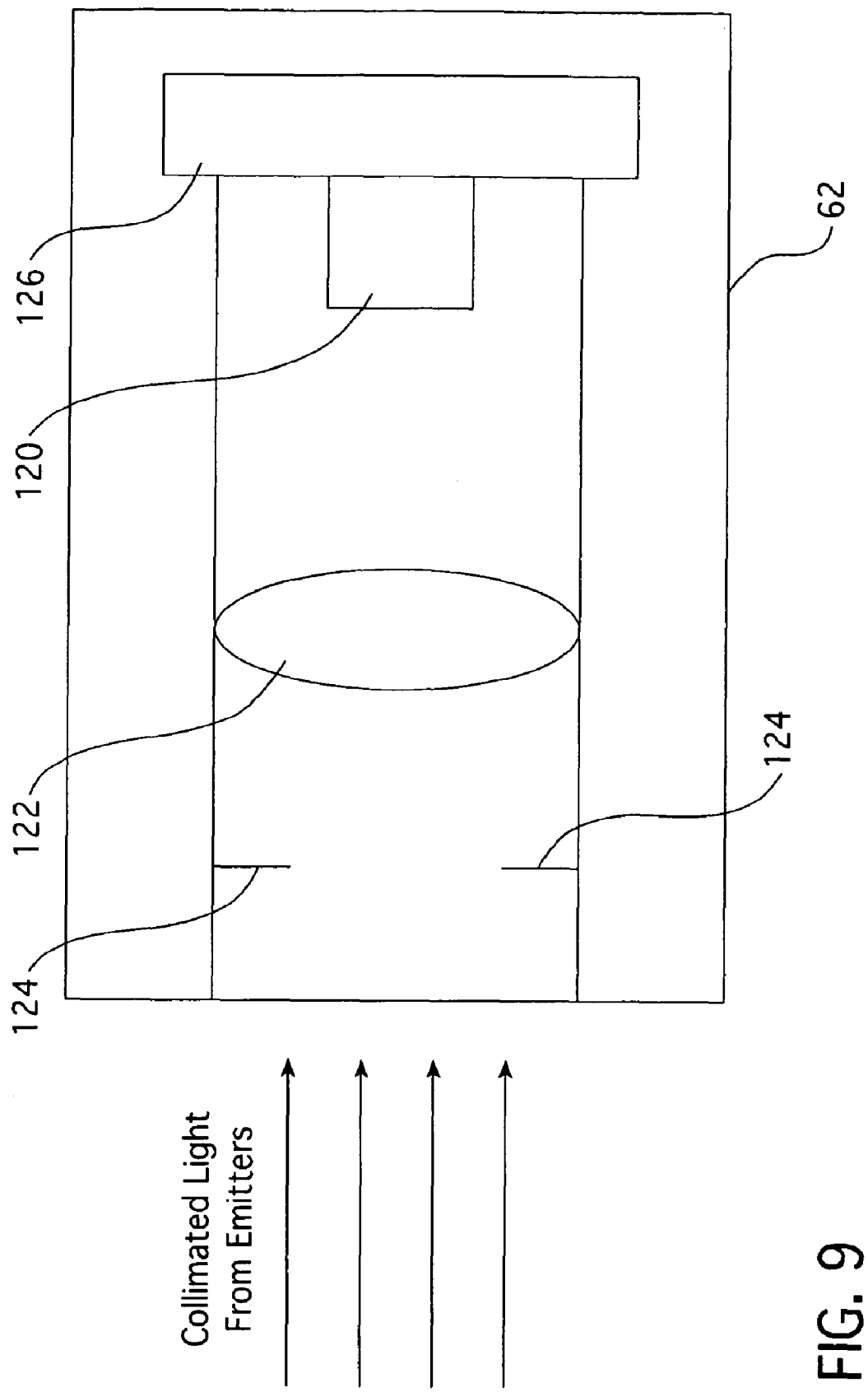
FIG. 9 shows a sensor of the inspection system according to various embodiments of the present invention.

FIG. 9 is a diagram of a sensor 62 according to various embodiments of the present invention. In the illustrated embodiment, the sensor 62 includes a broadband photodetector 120 for sensing the light energy from the emitter assemblies 60. According to various embodiments, the photodetector 120 may be an enhanced InGaAs photodetector. Such a photodetector is capable of sensing a broad range of wavelengths, including the wavelength bands emitted by the emitter assemblies 60. The sensor 62 may further comprise one or more lenses 122 for focusing the incoming light onto the photodetector 120. The detector may also comprise stray light baffles 124. Also, the photodetector 120 may have an associated circuit board 126 or other type of substrate to which photodetector 120 is mounted and which provides an interface for the electrical connections (not shown) to the photodetector 120.

Figure 10:
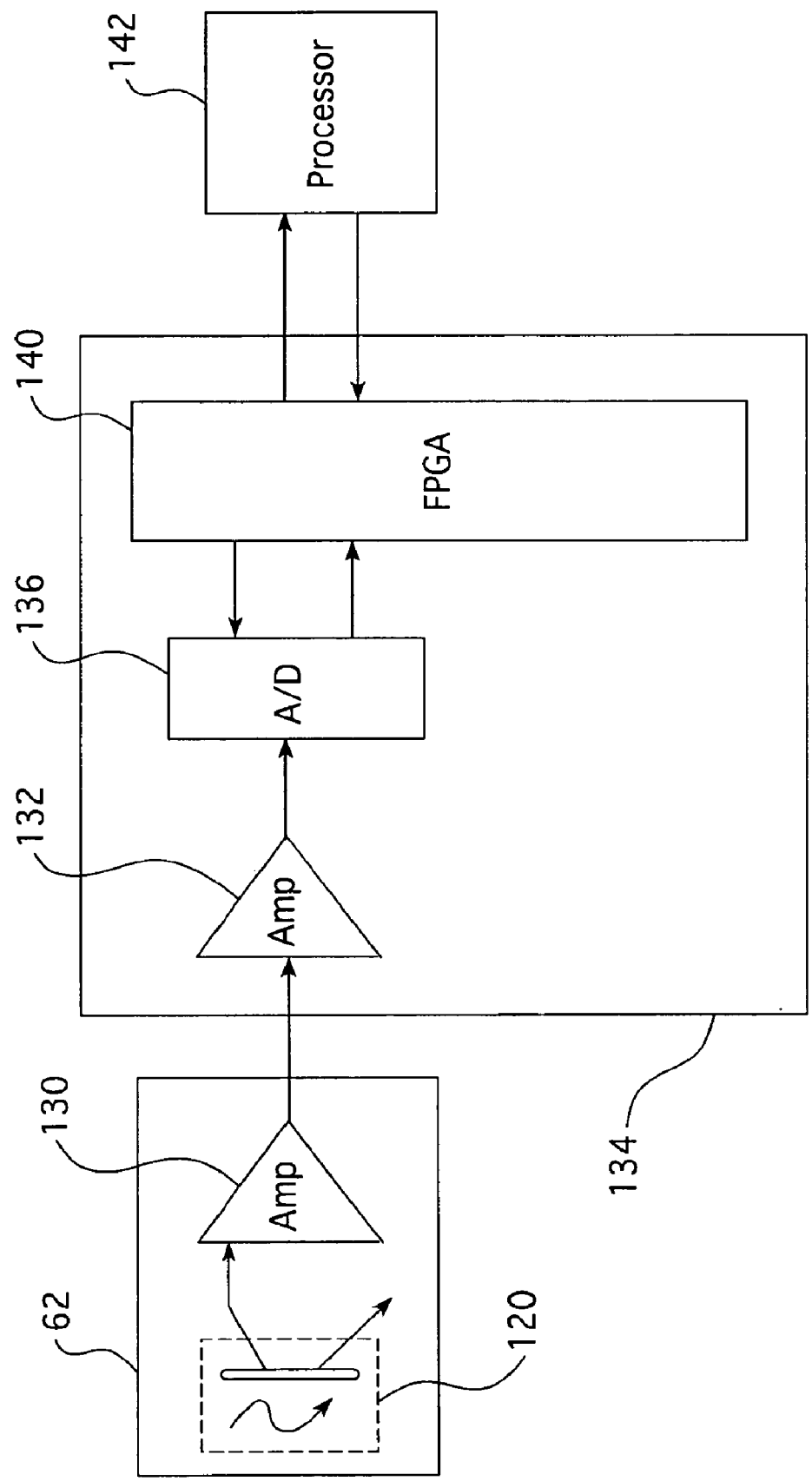
FIG. 10 is a simplified block diagram of a sensor circuit board of the inspection system according to various embodiments of the present invention.
Figure 11:
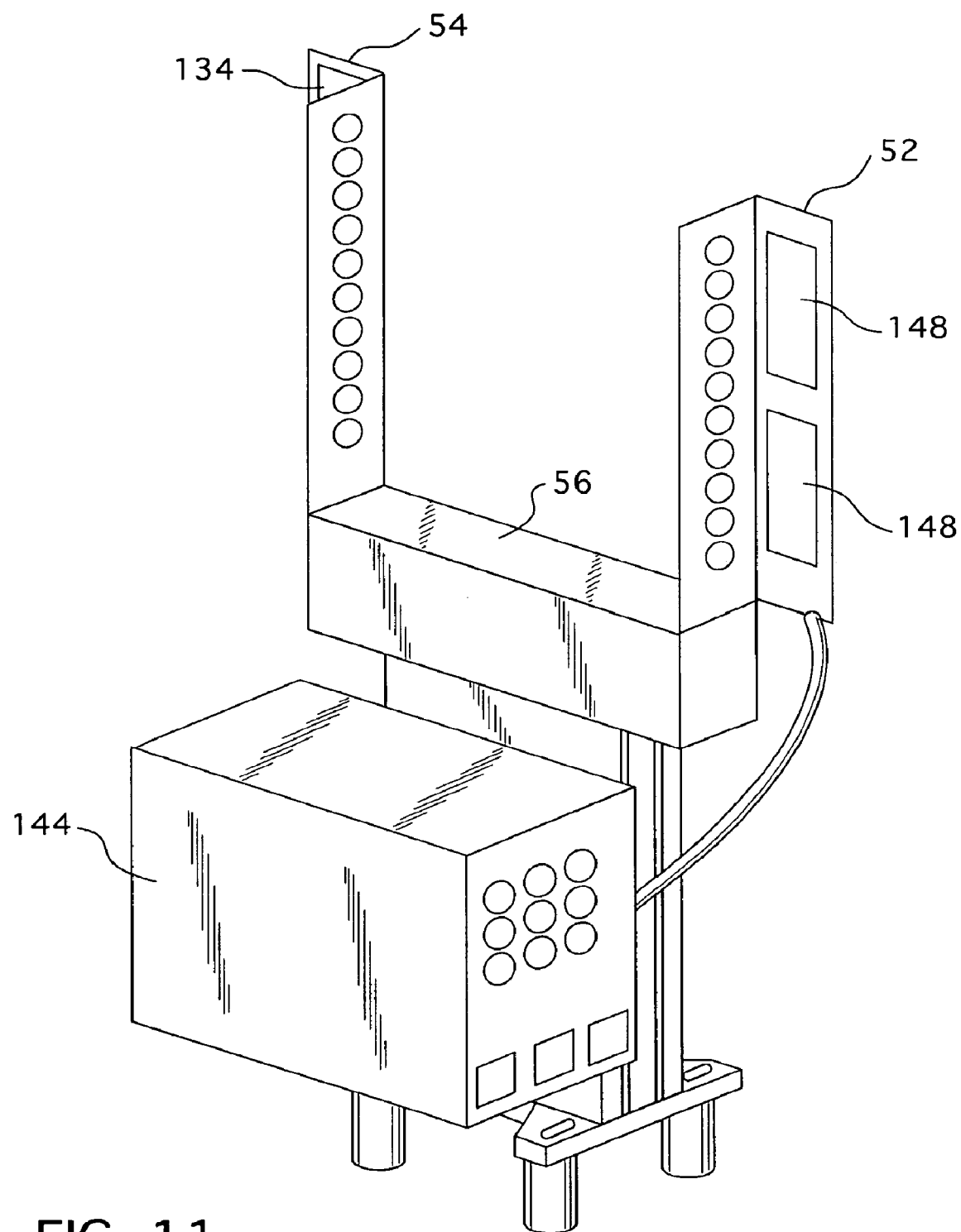

FIG. 10 is a simplified block diagram of the sensor 62 and an associated sensor controller circuit board 134. As shown in FIG. 10, the sensor 62 may further comprise a first amplifier 130 for amplifying the signal from the photodetector 120. The amplifier 130 may be integrated with the photodetector 120 or on the controller circuit board 126 (see FIG. 9). The output of the amplifier 130 may then be input to another amplifier 132 on the sensor circuit board 134. The sensor circuit board 134 may be located near the sensor 62, such as in the open space in the arm 54, as shown in FIG. 11. According to various embodiments, each circuit board 134 may interface with eight sensors 62 so that, for an embodiment having thirty two emitter-sensor pairs, there may be four such sensor circuit boards 134 for the thirty-two sensors.

As shown in FIG. 10, the circuit board 134 may comprise an analog-to-digital (A/D) converter 136 for converting the amplified analog signals from the photodetector 120 to digital form. According to various embodiments, the ND converter 136 may be a 16-bit A/D converter. The output from the A/D converter 136 may be input to a field programmable gate array (FPGA) 140 or some other suitable circuit, such as an ASIC. The circuit board 134 may communicate with a processor 142 via a LVDS (low voltage differential signaling) communication link, for example, or some other suitable connection (e.g., RS-232), using either serial or parallel data transmission. The processor 142 may be a digital signal processor or some other suitable processor for processing the signals from the sensors 62 as described herein. The processor 142 may have a single or multiple cores. One processor 142 may process the data from each of the circuit boards 134, or there may be multiple processors. The processor(s) 142 may be contained, for example, in an electrical enclosure 144 mounted under the crossbar section 68 of the inspection system 50, as shown in FIG. 11.

Figure 12:
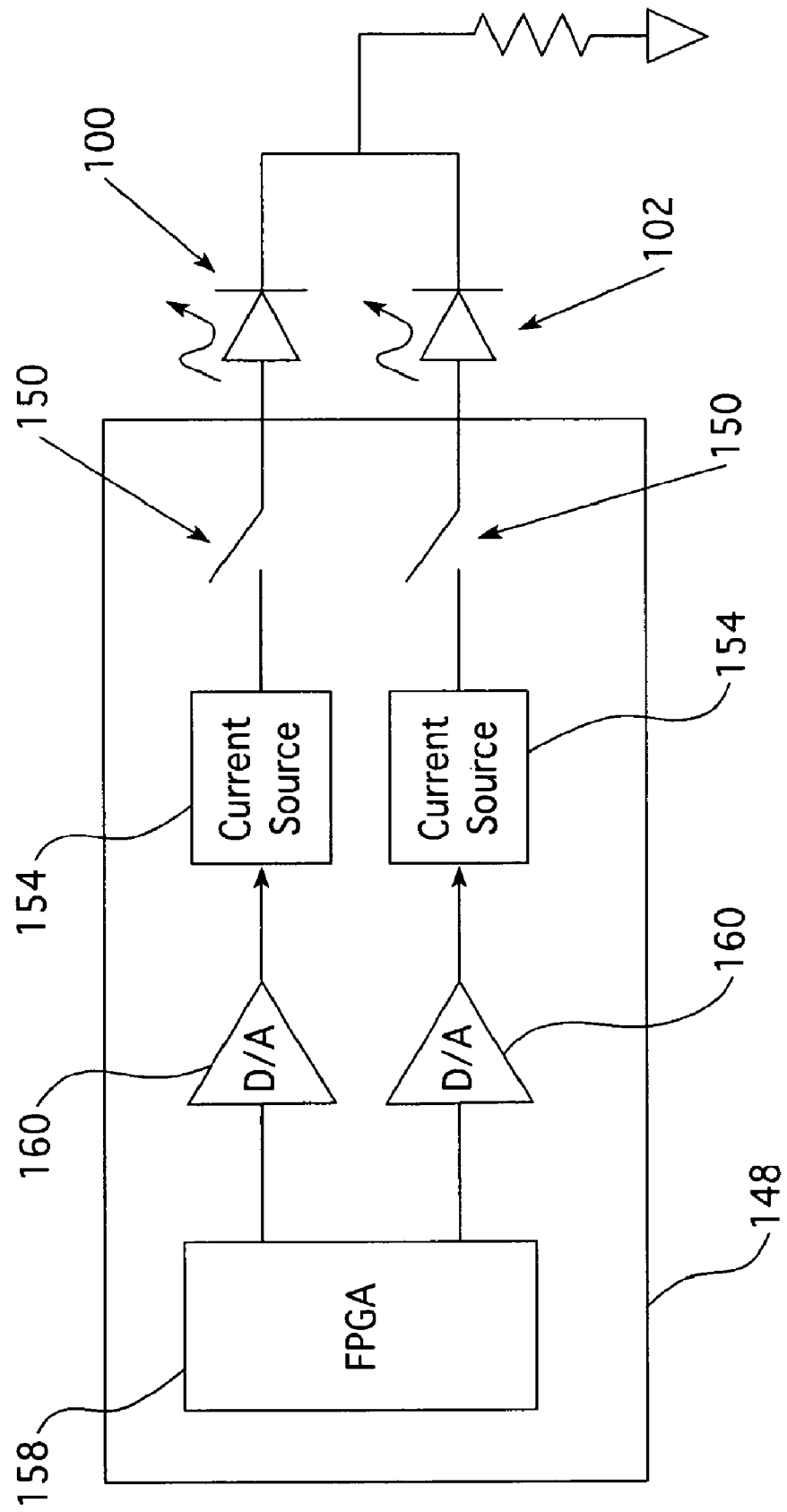
FIG. 12 is a simplified block diagram of a driver board for an emitter assembly 60 of the inspection system according to various embodiments of the present invention.

FIG. 12 is a simplified schematic diagram of a controller 148 for the emitter LEDs according to various embodiments. Each LED 100, 102 may have an associated switch 150, which may control when the LEDs are on and off. The switches 150 may be implemented as field effector transistors (FETs), for example. An adjustable constant current source 154 may drive the LEDs 100, 102. The current from the current sources 154 may be adjusted to control the light intensity of the LEDs 100, 102 for calibration purposes, for example. Any suitable adjustable current source may be used, such as a transistor current source or a current mirror. The current sources 154 may be controlled by signals from a FPGA 158 (or some other suitable programmable circuit) via a digital-to-analog (D/A) converter 160. The FPGA 158 may store values to appropriately compensate the intensity levels of the LEDs 100, 102 based on feedback from the processor(s) 142.

According to various embodiments, the FPGA 158 may control the LEDs for numerous emitter assemblies 60. For example, a single FPGA 158 could control eight emitter assemblies 60, each having two LEDs, as described above. The FPGA 158 along with the D/A converter 160, current sources 154, and switches 150 for each of the eight channels could be contained on a circuit board near the emitter assemblies 60, such as in the space defined by the frame 68 of the arm 52, as shown in FIG. 11. For an embodiment having thirty-two emitter assemblies 60, therefore, there could be four such controller circuit boards 148. The FPGAs 158 may communicate with the processor 142 in the enclosure (see FIG. 11) using a LVDS connection or some other suitable serial or parallel communication link.

Figure 13:
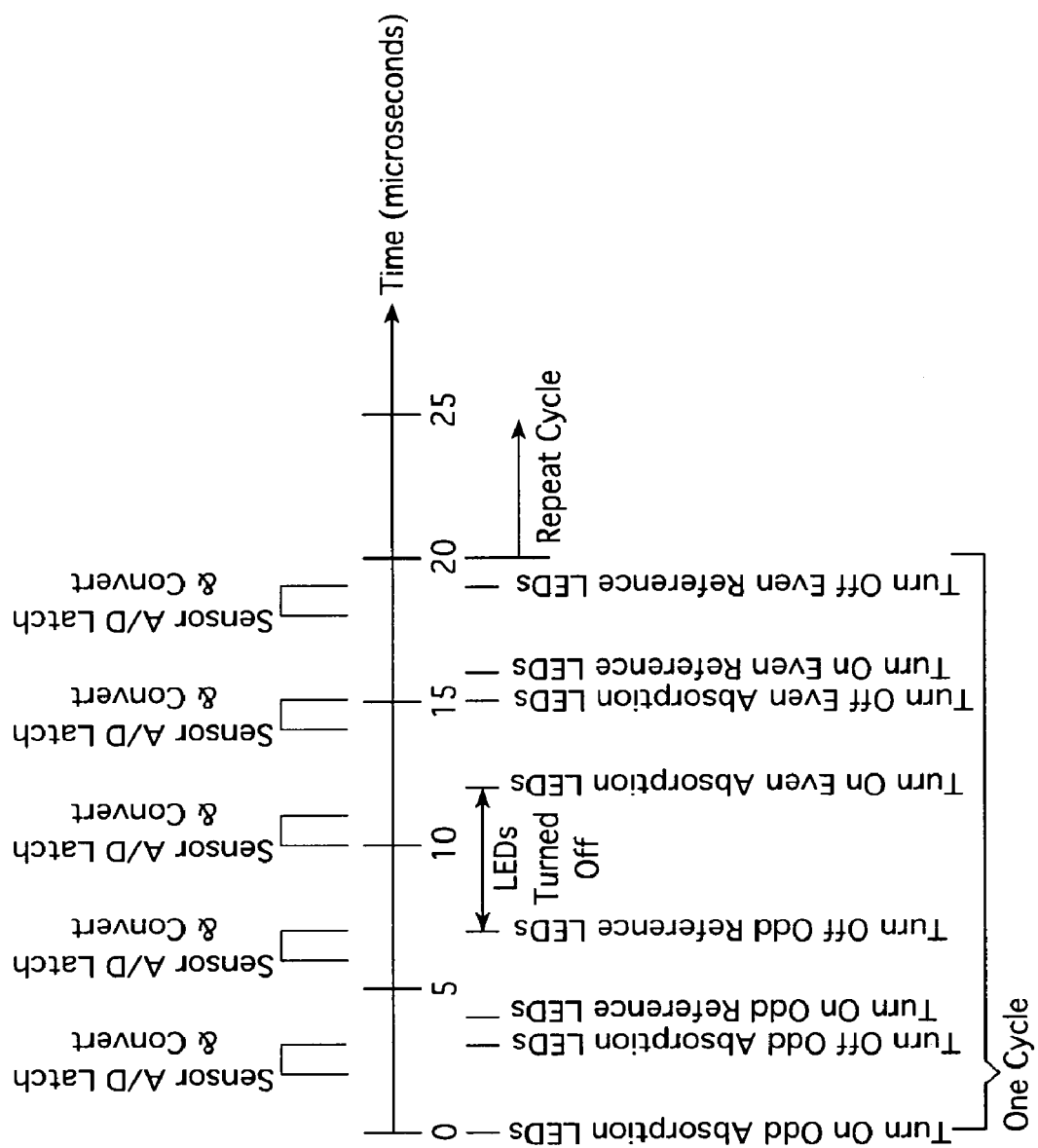
FIG. 13 is a timing diagram according to various embodiments of the present invention.

According to various embodiments, the LEDs 100, 102 may be switched on and off cyclically. During a time period when both LEDs 100, 102 are off, the drive for the LEDs 100, 102 may be adjusted and/or the gain of the amplifiers 130, 132 on the sensor side may be adjusted to compensate for drifts in performance and/or to otherwise keep the emitter-sensor pairs calibrated. FIG. 13 is a timing diagram showing the system timing architecture for a sampling cycle according to various embodiments of the present invention. In the illustrated embodiment, the switching cycle has a duration of 20 microseconds, corresponding to a sampling rate of 50 kHz. Of course, in other embodiments, switching cycles having different durations could be used.

The LEDs 100, 102 of the emitter assemblies 60 preferably take less than 500 nanoseconds to turn on, and the photodetectors 120 of the sensors preferably have a response time of 500 nanoseconds or less. Further, the recovery time of the photodetectors 120 after turn off is preferably 500 nanoseconds or less. As shown in the example of FIG. 13, at the start of the cycle (t=0), the absorption LED in every other emitter assembly 60 (e.g., the "odd" ones) is turned on. Since the sensors 62 may detect light energy from more than one emitter assembly 60, the emitter assemblies 60 may be turned on and off in banks in such a fashion. In the illustrated embodiment, the emitter assemblies 60 are operated it two banks (odd and even), although in other embodiments the emitter assemblies could be operated in more than two banks.

During the approximate time interval from t=2 to 3 microseconds, the ND converter 136 (see FIG. 10) for each sensor 62 may latch and convert the signal from the photodetector 120 for this condition (the odd absorption LEDs being on). At t=3 microseconds, the odd LEDs may be turned off, and at t=4 microseconds the odd reference LEDs may be turned on. During the approximate time interval from t=6 to 7 microseconds, the A/D converter 136 for each sensor 62 may latch and convert the signal from the photodetector 120 for the condition when the odd reference LEDs are on. At t=7 microseconds, the odd reference LEDs may then be turned off.

From t=7 microsecond to t=12 microsecond, all of the LEDs of the emitter assemblies may be turned off. During the approximate time interval from t=10 to 11 microseconds, the A/D converter 136 for each sensor 62 may latch and convert the signal from the photodetector 120 for the condition when the all of the LEDs are off. At time t=12 microseconds, the "even" absorption LEDs (i.e., the ones that were not turned on at t=0 microseconds) are turned on. During the approximate time interval from t=14 to 15 microseconds, the A/D converter 136 for each sensor 62 may latch and convert the signal from the photodetector 120 for the condition when the even absorption LEDs are on. At t=15 microseconds the even absorption LEDs are turned off, and at t=16 microseconds the even reference LEDs are turned on. During the approximate time interval from t=18 to 19 microseconds, the ND converter 136 for each sensor 62 may latch and convert the signal from the photodetector 120 for the condition when the even reference LEDs are on. At t=19 microseconds, the even references LEDs are turned off. The cycle may then be repeated starting at t=20 microseconds, and so on.

According to various embodiments where a blow molder system (such as blow molder system 4 of FIG. 1) is used to fabricate the plastic containers, multiple sensors that are within or operatively associated with the blow molder system may provide information to a processor (such as processor 142) to enable synchronization of the specific molds and spindles in the blow molder which made the container being inspected and thereby provide valuable feedback information. One sensor, designated the blow-molder machine step sensor, may emit a signal which contains information regarding the counting of the molds and spindles from their corresponding starting position. The total number of molds or spindles may vary depending upon the make and model of blow-molder, but this information is known in advance. This information may be programmed into the system. A second signal, which is from the blow-molder synchronization sensor, may provide information regarding start of a new cycle of rotating the mold assembly. The blow-molder spindle synchronizing sensor provides output regarding the new cycle of rotating the spindle assembly. The sensors employed for monitoring machine step mold sync and spindle sync may be positioned at any suitable location within the blow-molder and may be of any suitable type, such as inductive sensors which are well known to those skilled in the art.

A part-in-place sensor may provide a signal to the processor(s) 142 indicating that a container has arrived at the inspection system 20 and that the light-energy-based inspection should be initiated. At that point, the container transects the beams of emitted light from the multiple discrete-wavelength spectral light sources 60. The processor(s) 142 is in communication with the broadband sensors 62 and receives electrical signals from the sensors 62, as described above, in order to perform a comparison of the thickness information contained within the electrical signals with stored information regarding desired thickness. More details regarding such sensors are described in U.S. Pat. No. 6,863,860, which is incorporated herein by reference.

According to various embodiments, if the thickness is not within the desired range, the processor(s) 142 may emits a signal or command to a blow-molder reject mechanism 26, which in turn initiates a rejection signal to operate a container rejection system and discard that container from the conveyer.

Figure 14:
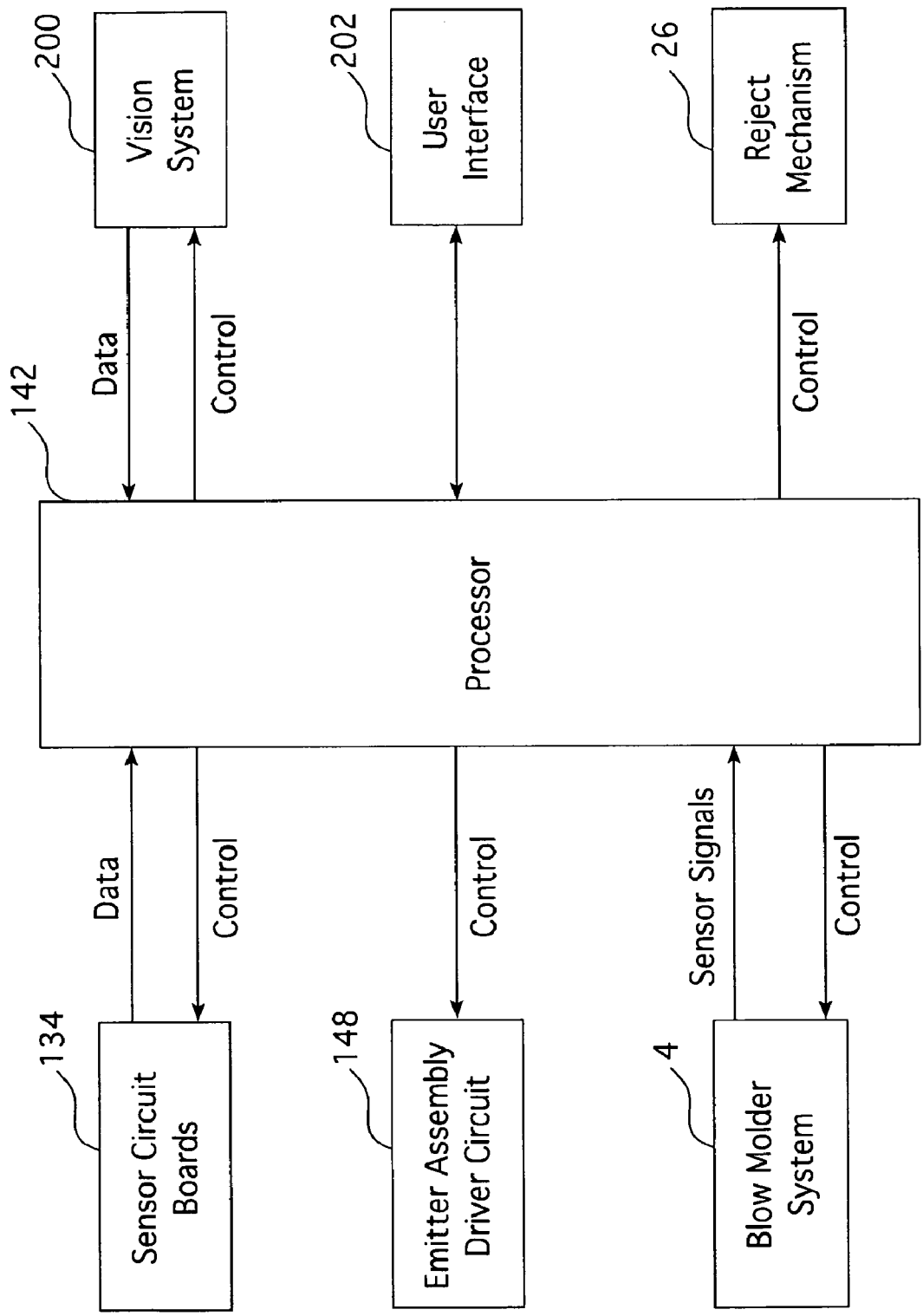
FIG. 14 is a simplified block diagram of the inspection system according to various embodiments of the present invention.

FIG. 14 is a diagram illustrating the processor-based control system that may be realized using the inspection system 50 according to various embodiments. The signals from the photodetectors 120/sensor circuit boards 134 are input to the processor 142, including the signals for the conditions when only the absorption LEDs are on, when only the reference LEDs are on, and when all of the LEDs are off. Based on this information, the processor 142 can compute or determine the average thickness through 2 sidewalls of the container 66 at each height level of the emitter-sensor pairs. Thus, for example, if there are thirty-two emitter-sensor pairs, the processor 142 can compute the average thickness through 2 sidewalls of the container 66 at thirty-two different height levels on the bottle. This information can be used to determine if a container should be rejected. If a container is to be rejected, the processor 142 may be programmed to send a reject signal to the reject mechanism 26 to the cause the container to be rejected.

The processor 142 could also compute the mass, volume and/or material distribution of the container as these attributes (or characteristics) are related to thickness. The mass or volume of various sections of the inspected container, e.g., sections corresponding to the various height levels of the emitter-sensor pair, could also be calculated by the processor. The processor could also compute container diameter by measuring the time between detection of the leading edge of the container and detection of the trailing edge. This time interval, when combined with container velocity information, provides an indication of container diameter at multiple elevations, sufficient for identification of malformed containers.

The processor 142 may be programmed to also calculate trending information, such as the average thickness at each height level for the last x containers and/or the last y seconds. Also, other relevant, related statistical information (e.g., standard deviation, etc.) could be calculated. Based on this information, the processor 142 may be programmed to, for example, send a control signal to the preform oven 2 to modify the temperature of its heaters (e.g., raise or lower the temperature).

The processor 142 may be programmed to also calculate updated calibration data for the emitter assemblies 60 and the sensors 62 based on the signals from the sensor circuit boards 134. For example, the processor 142 may be programmed to compute whether the drive signal from the current sources 154 for the emitter assemblies 60 must be adjusted and/or whether the gain of either of the amplifier stages 130, 132 of the sensor circuit board 134 must be adjusted. The processor 142 may be programmed to transmit the calibration adjustment signals to one or more of the FPGAs 158 of the driver boards 148 for the emitter assemblies 60 and, based on calibration values coded into the FPGAs 158, the FPGAs 158 may control the drive signal from the current source 154. Similarly, the processor may transmit calibration adjustment signals to the FPGAs 140 of the sensor circuit boards 134 and, based on calibration values coded into the FPGAs 140, the FPGAs 140 may control the gain of the amplifier stages 130, 132 to maintain calibration.

Also, based on the mold-spindle timing sensor information from the blow molder 6, as described above, the processor 142 could calculate the average thickness at each height level for the last x containers for a specified mold, spindle, and/or mold-spindle combination. The processor 142 could also calculate other related statistical information that may be relevant. This information may be used to detect a defective mold or spindle, or to adjust a parameter of the blow molder 6.

The system may also include, in some embodiments, a vision system 200 for inspecting the formed containers. The vision system 200 may comprise one or more cameras to capture images of the formed containers either from the top, bottom, and/or sides. These images may be passed to the processor 142 and analyzed to detect defects in the formed containers. If a container with defects is detected, the processor 142 may be programmed to send a signal to the reject mechanism to reject the container. The vision system could be similar to the vision system used in the AGR TopWave Pet-Wall Plus thickness monitoring system or as described in U.S. Pat. No. 6,967,716, which is incorporated herein by reference.

The output thickness information from the processor(s) 142, as well as the vision-based information for a system that includes a vision system 200, may be delivered to a graphical user interface 202, such as a touch screen display. The GUI 202 may provide an operator with information regarding specific containers produced by particular mold and spindle combinations of the blow molder. It is preferred that the values be averaged over a period of time, such as a number of seconds or minutes. In addition or in lieu of time measurement, the average may be obtained for a fixed number of containers which may be on the order of 2 to 2500. The GUI 202 may also provide trend information for the blow-molder and individual molds and spindles. In the event of serious problems requiring immediate attention, visual and/or audio alarms may be provided. In addition, the operator may input certain information to the processor 142 via the GUI 202 to alter calibrations in order to control operation of the processor(s). Also, the operator may input process limits and reject limits into the processor(s) 142 for each of the thickness measurement zones of the containers to be inspected. The reject limits are the upper and lower thickness values that would trigger the rejection of a container. The process limits are the upper and lower values for the time-averaged or number of container averaged thickness that would trigger a process alarm indicator.

According to various embodiments, in addition to or in lieu of LEDs, the light emitter assemblies 60 may use one or more laser diodes to emit light energy at the discrete wavelength bands. Also, instead of a dichroic beam splitter 84 in the emitter assemblies 60 to merge the discrete narrow band light sources, other optical techniques could be used to achieve the same effect. For instance, a bifurcated fiber optic coupler may used to mix the light energy from the two discrete light sources.

Figure 15:
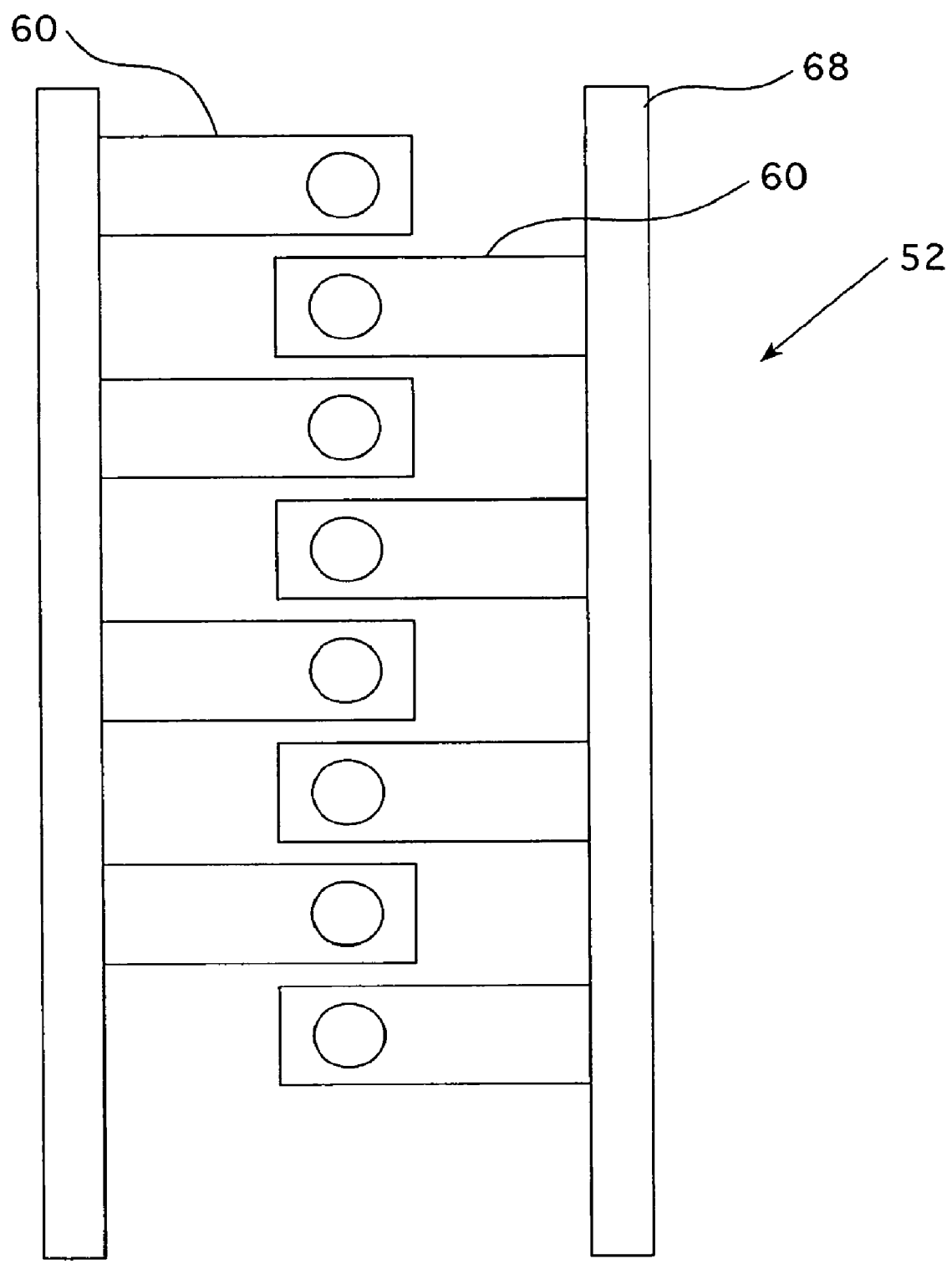
FIG. 15 shows a staggered vertical array of emitter assemblies according to various embodiments of the present invention.

Although the preferred embodiment uses enhanced InGaAs photodetectors 120, in other embodiments other types of detectors could be used to the same effect. For instance, PbS detectors could be used to measure a broad range of light in the relevant wavelength ranges. In addition, although the above-described embodiments use vertically aligned LEDs and sensors, an alternative configuration would stagger the mounting of adjacent LEDs/sensor pairs in order to achieve a more densely stacked vertical array of sensors, as shown in the example of FIG. 15, which just shows a staggered vertical array of emitter assemblies 60. In various embodiments, the photodetectors could be similarly staggered.

The examples presented herein are intended to illustrate potential and specific implementations of the embodiments. It can be appreciated that the exemplary embodiments are intended primarily for purposes of illustration for those skilled in the art. No particular aspect or aspects of the examples is/are intended to limit the scope of the described embodiments.

As used in the claims, the term "plastic container(s)" means any type of container made from any type of plastic material including polyvinyl chloride, polyethylene, polymethyl methacrylate, polyurethanes, thermoplastic, elastomer, PET, or polyolefin, unless otherwise specifically noted.

It is to be understood that the figures and descriptions of the embodiments have been simplified to illustrate elements that are relevant for a clear understanding of the embodiments, while eliminating, for purposes of clarity, other elements. For example, certain operating system details and power supply-related components are not described herein. Those of ordinary skill in the art will recognize, however, that these and other elements may be desirable in inspection systems as described hereinabove. However, because such elements are well known in the art and because they do not facilitate a better understanding of the embodiments, a discussion of such elements is not provided herein.

In general, it will be apparent to one of ordinary skill in the art that at least some of the embodiments described herein may be implemented in many different embodiments of software, firmware and/or hardware. The software and firmware code may be executed by a processor (such as the processor 142) or any other similar computing device. The software code or specialized control hardware which may be used to implement embodiments is not limiting. The processors and other programmable components disclosed herein may include memory for storing certain software applications used in obtaining, processing and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable media.

In various embodiments disclosed herein, a single component may be replaced by multiple components and multiple components may be replaced by a single component, to perform a given function or functions. Except where such substitution would not be operative, such substitution is within the intended scope of the embodiments. For example, processor 142 may be replaced with multiple processors.

While various embodiments have been described herein, it should be apparent that various modifications, alterations and adaptations to those embodiments may occur to persons skilled in the art with attainment of at least some of the advantages. The disclosed embodiments are therefore intended to include all such modifications, alterations and adaptations without departing from the scope of the embodiments as set forth herein.

What is claimed is:

1. A system for measuring a property of a blow-molded container, the system comprising:
    a plurality of emitters, wherein at least a first portion of the plurality of emitters is configured to emit light energy at a first wavelength band and at least a second portion of the plurality of emitters is configured to emit light energy at a second wavelength band as the container passes through an inspection area, wherein the plurality of emitters are configured such that emissions in the same wavelength band from spatially adjacent emitters are offset in time;
    a plurality of detectors, wherein each of the plurality of detectors is aligned to receive light energy emitted by at least one of the plurality of emitters and is sensitive to light energy in the first wavelength band and in the second wavelength band; and
    at least one processor in communication with the plurality of emitters and the plurality of detectors, wherein the at least one processor is programmed to:
        receive from the plurality of detectors a first signal indicating light energy in the first wavelength band received by at least one of the plurality of detectors through the blow-molded container;
        receive from the plurality of detectors a second signal indicating light energy in the second wavelength band received by at least one of the plurality of detectors through the blow-molded container; and
        determine a characteristic of the blow-molded container considering the first signal and the second signal.

2. The system of claim 1, wherein all of the plurality of emitters are configured to alternately emit light energy at the first wavelength band and at the second wavelength band.

3. The system of claim 1, wherein light energy in the first wavelength band is at least partially absorbed by the blow-molded container, and wherein light energy in the second wavelength band is substantially transmitted by the blow-molded container.

4. The system of claim 1, wherein the first signal is indicative of light in the first wavelength band absorbed by the blow-molded container.

5. The system of claim 1, wherein the plurality of emitters are arranged vertically.

6. The system of claim 5, wherein the plurality of detectors are arranged vertically.

7. The system of claim 1, wherein the characteristic of the blow-molded container is a two-wall average thickness of the container.

8. The system of claim 1, wherein the characteristic of the blow-molded container is selected from the group consisting of mass and volume.

9. The system of claim 1, wherein each emitter comprises:
    a first light source that emits light energy in the first wavelength band; and
    a second light source that emits light energy in the second wavelength band.

10. The system of claim 1, wherein physically adjacent emitters of the plurality of emitters do not emit light energy simultaneously.

11. The system of claim 1, wherein the first wavelength band is around 1835 nm and the second wavelength band is around 2350 nm.

12. The system of claim 1, wherein the first wavelength band has a bandwidth less than or equal to 200 nm full width at half maximum.

13. The system of claim 1, wherein each of the plurality of emitters comprises at least one of a light emitting diode (LED) and a laser diode.

14. The system of claim 1, wherein at least one of the plurality of detectors comprises an InGaAs photodetector.

15. A system for blow-molding containers, the system comprising:
    an oven for heating blow-molded container performs;
    a blow molder for molding the heated performs into blow-molded containers; and
    an inspection system for measuring a property of the blow-molded containers as the blow-molded containers pass through an inspection area after molding by the blow molder, the inspection system comprising:
        a plurality of emitters, wherein at least a first portion of the plurality of emitters is configured to emit light energy at a first wavelength band and at least a second portion of the plurality of emitters is configured to emit light energy at a second wavelength band, wherein the plurality of emitters are configured such that emissions in the same wavelength band from spatially adjacent emitters are offset in time;
        a plurality of detectors, wherein each of the plurality of detectors is aligned to receive light energy emitted by at least one of the plurality of emitters and is sensitive to light energy in the first wavelength band and in the second wavelength band; and
        at least one processor in communication with the plurality of emitters and the plurality of detectors, wherein the processor is programmed to:
            receive from the plurality of detectors a first signal indicating light energy in the first wavelength band received by at least one of the plurality of detectors through the blow-molded container;

receive from the plurality of detectors a second signal indicating light energy in the second wavelength band received by at least one of the plurality of detectors through the blow-molded container; and determine a characteristic of the blow-molded container considering the first signal and the second signal.

16. The system of claim 15, wherein the at least one processor is further programmed to send a control signal to the oven to change a parameter of the oven based on the characteristic determined by the at least one processor.

17. The system of claim 15, wherein the at least one processor is further programmed to send a control signal to the blow molder to change a parameter of the blow molder based on the characteristic determined by the at least one processor.

18. A method of measuring a property of a blow-molded container, the method comprising:

emitting light energy at a first wavelength band through a blow-molded container as the blow-molded container passes through an inspection area using at least a portion of a plurality of emitters, wherein emissions at the first wavelength band from spatially adjacent emitters are offset in time;

detecting the light energy in the first wavelength band transmitted through the blow-molded container;

emitting light energy at a second wavelength band through the blow-molded container;

detecting the light energy in the second wavelength band transmitted through the blow-molded container; and determining a characteristic of the blow-molded container considering the light energy in the first wavelength band transmitted through the blow-molded container and the light energy in the second wavelength band transmitted through the blow-molded container.

19. The method of claim 18, wherein the emitting light energy in the first wavelength band and the emitting light energy in the second wavelength band is performed by a plurality of emitters.

20. The method of claim 18, wherein the detecting the light energy in the first wavelength band and the detecting the light energy in the second wavelength band is performed by a plurality of detectors, wherein each detector of the plurality of detectors is sensitive to light energy in the first wavelength band and in the second wavelength band.

21. A method of manufacturing a blow-molded container, the method comprising:

heating a preform with a preform oven;

forming a blow-molded container from the heated preform by a blow-molder;

emitting light energy at a first wavelength band through the blow-molded container as the blow-molded container passes through an inspection area after formation of the blow-molded container by the blow-molder using at least a portion of a plurality of emitters, wherein emissions at the first wavelength band from spatially adjacent emitters are offset in time;

detecting the light energy in the first wavelength band transmitted through the blow-molded container;

emitting light energy at a second wavelength band through the blow-molded container;

detecting the light energy in the second wavelength band transmitted through the blow-molded container; and determining a characteristic of the blow-molded container considering the light energy in the first wavelength band transmitted through the blow-molded container and the light energy in the second wavelength band transmitted through the blow-molded container.

22. The method of claim 21, wherein the emitting light energy in the first wavelength band and the emitting light energy in the second wavelength band is performed by a plurality of emitters.

23. The method of claim 21, wherein the detecting the light energy in the first wavelength band and the detecting the light energy in the second wavelength band is performed by a plurality of detectors, wherein each detector of the plurality of detectors is sensitive to light energy in the first wavelength band and in the second wavelength band.

24. The method of claim 21, further comprising changing a parameter of the oven based on the characteristic.

25. The method of claim 22, further comprising changing a parameter of the blow molder based on the characteristic.

* * * * *